(12) United States Patent
Matsuzaki

(10) Patent No.: US 8,987,317 B2
(45) Date of Patent: Mar. 24, 2015

(54) PLANT DISEASE CONTROL COMPOSITION AND ITS USE

(75) Inventor: Yuichi Matsuzaki, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 82 days.

(21) Appl. No.: 13/643,783

(22) PCT Filed: Apr. 25, 2011

(86) PCT No.: PCT/JP2011/002422
§ 371 (c)(1), (2), (4) Date: Nov. 13, 2012

(87) PCT Pub. No.: WO2011/135839
PCT Pub. Date: Nov. 3, 2011

(65) Prior Publication Data
US 2013/0210882 A1    Aug. 15, 2013

(30) Foreign Application Priority Data

Apr. 28, 2010 (JP) ................................ 2010-104099

(51) Int. Cl.
A01N 43/56 (2006.01)
A01N 47/14 (2006.01)
A01N 47/26 (2006.01)
A01N 55/02 (2006.01)

(52) U.S. Cl.
CPC ............... *A01N 43/56* (2013.01); *A01N 47/26* (2013.01); *A01N 55/02* (2013.01)
USPC .......................................... 514/406; 514/491

(58) Field of Classification Search
None
See application file for complete search history.

(56) References Cited

U.S. PATENT DOCUMENTS

| | | | |
|---|---|---|---|
| 4,536,506 A | 8/1985 | Marcoux et al. | |
| 4,742,074 A | 5/1988 | Nishida et al. | |
| 5,093,347 A | 3/1992 | Graneto et al. | |
| 5,948,819 A | 9/1999 | Ohtsuka et al. | |
| 7,232,836 B2 | 6/2007 | Lahm et al. | |
| 7,612,100 B2 | 11/2009 | Koyanagi et al. | |
| 7,902,231 B2 | 3/2011 | Lahm et al. | |
| 7,994,201 B2 | 8/2011 | Koyanagi et al. | |
| 8,148,521 B2 | 4/2012 | Lahm et al. | |
| 8,158,802 B2 | 4/2012 | Lahm et al. | |
| 2009/0123561 A1 | 5/2009 | Gewehr et al. | |
| 2009/0181956 A1 | 7/2009 | Ikegami et al. | |
| 2010/0120866 A1 | 5/2010 | Nokura et al. | |
| 2011/0257231 A1 | 10/2011 | Koyanagi et al. | |
| 2012/0171183 A1 | 7/2012 | Lahm et al. | |

FOREIGN PATENT DOCUMENTS

| | | |
|---|---|---|
| JP | 62-96472 A | 5/1987 |
| JP | 3729825 B2 | 12/2005 |
| JP | 2007-182422 A | 7/2007 |
| JP | 4150379 B2 | 9/2008 |
| JP | 2008-280335 A | 11/2008 |
| JP | 2009-502747 A | 1/2009 |
| JP | 2010-13389 A | 1/2010 |
| JP | 2010-83869 A | 4/2010 |
| JP | 2010-83883 A | 4/2010 |
| WO | WO 86/02641 A1 | 5/1986 |
| WO | WO 92/12970 A1 | 8/1992 |
| WO | WO 95/27693 A1 | 10/1995 |
| WO | WO 2004/067528 A1 | 8/2004 |
| WO | WO 2005/077934 A1 | 8/2005 |
| WO | WO 2007/095229 A2 | 8/2007 |
| WO | WO 2007/108483 A1 | 9/2007 |
| WO | WO 2008/046533 A2 | 4/2008 |
| WO | WO 2008/126933 A2 | 10/2008 |
| WO | WO 2009/119872 A2 | 10/2009 |
| WO | WO 2010/021404 A2 | 2/2010 |
| WO | WO 2010/024365 A1 | 3/2010 |
| WO | WO 2010/024422 A1 | 3/2010 |

OTHER PUBLICATIONS

International Search Report for International Patent Application No. PCT/JP2011/002422, dated May 31, 2011.
Delp, "Coping with Resistance to Plant Disease," Plant Disease, vol. 64, No. 7, Jul. 1980, pp. 652-657.

(Continued)

*Primary Examiner* — Bethany Barham
*Assistant Examiner* — Barbara Frazier
(74) *Attorney, Agent, or Firm* — Birch, Stewart, Kolasch & Birch, LLP

(57) ABSTRACT

A plant disease control composition comprising a carboxamide compound represented by following formula (I), wherein $R^1$ represents a hydrogen atom or a methyl group, and $R^2$ represents a methyl group, a difluoromethyl group or a trifluoromethyl group, and one or more dithiocarbamate compounds selected from group (A) consisting of mancozeb, maneb, thiram and zineb is provided by the present invention, and this composition has an excellent effect for controlling a plan disease.

(I)

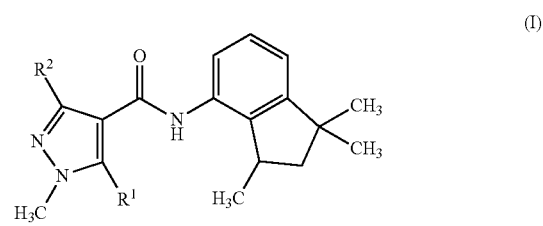

3 Claims, No Drawings

(56) References Cited

OTHER PUBLICATIONS

International Search Report for International Patent Application No. PCT/JP2011/002410, dated Jun. 28, 2011.
International Search Report for International Patent Application No. PCT/JP2011/002411, dated Jul. 5, 2011.
International Search Report for International Patent Application No. PCT/JP2011/002413, dated Jul. 19, 2011.
International Search Report for International Patent Application No. PCT/JP2011/002414, dated Jul. 12, 2011.
International Search Report for International Patent Application No. PCT/JP2011/002415, dated Jul. 19, 2011.
International Search Report for International Patent Application No. PCT/JP2011/002416, dated May 31, 2011.
International Search Report for International Patent Application No. PCT/JP2011/002417, dated Jul. 26, 2011.
International Search Report for International Patent Application No. PCT/JP2011/002418, dated May 31, 2011.
International Search Report for International Patent Application No. PCT/JP2011/002419, dated May 31, 2011.
International Search Report for International Patent Application No. PCT/JP2011/002420, dated May 31, 2011.
International Search Report for International Patent Application No. PCT/JP2011/002421, dated May 31, 2011.
International Search Report for International Patent Application No. PCT/JP2011/002423, dated Jul. 19, 2011.
Office Action for U.S. Appl. No. 13/643,576, dated Jun. 12, 2013.
Office Action for U.S. Appl. No. 13/643,577, dated Jun. 11, 2013.
Office Action for U.S. Appl. No. 13/643,818, dated Aug. 20, 2013.
Office Action for U.S. Appl. No. 13/643,846, dated Aug. 7, 2013.
Office Action for U.S. Appl. No. 13/643,913, dated Apr. 26, 2013.
Office Action for U.S. Appl. No. 13/643,960, dated Aug. 1, 2013.

PLANT DISEASE CONTROL COMPOSITION AND ITS USE

TECHNICAL FIELD

The present invention relates to a plant disease control composition and its use.

BACKGROUND ART

Many compounds have been developed for controlling plant diseases and actually used (see, for example, PTL 1 and 2).

CITATION LIST

Patent Literature

[PTL 1]: WO86/02641
[PTL 2]: WO92/12970

SUMMARY OF INVENTION

Technical Problem

An object of the present invention is to provide a composition having an excellent effect for controlling plant disease.

Solution to Problem

The inventor of the present invention studied for seeking a composition having an excellent effect for plant disease and found that a composition comprising a carboxamide compound represented by following formula (I) and one or more dithiocarbamate compounds selected from following group (A) has an excellent effect for controlling plant disease and then completed the present invention.

The present invention provides the following [1] to [5].

A plant disease control composition comprising a carboxamide compound represented by formula (I):

[Chem.1]

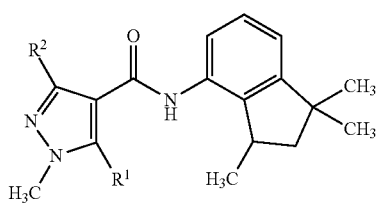

(I)

wherein
$R^1$ represents a hydrogen atom or a methyl group, and
$R^2$ represents a methyl group, a difluoromethyl group or a trifluoromethyl group,
and one or more dithiocarbamate compounds selected from group (A) consisting of mancozeb, maneb, thiram and zineb.

The plant disease control composition according to above [I], wherein the weight ratio of the carboxamide compound to dithiocarbamate compound(s) is from 0.01/1 to 1/1 of the carboxamide compound/the dithiocarbamate compound(s).

A method of controlling plant disease which comprises a step of treating a plant or the soil where a plan grows with an effective amount of a carboxamide compound represented by formula (I):

[Chem.2]

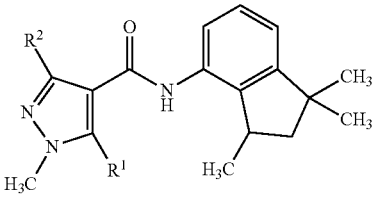

(I)

wherein
$R^1$ represents a hydrogen atom or a methyl group, and
$R^2$ represents a methyl group, a difluoromethyl group or a trifluoromethyl group, and one or more dithiocarbamate compounds selected from group (A) consisting of mancozeb, maneb, thiram and zineb.

The method of controlling plant disease according to above [3], wherein the weight ratio of the carboxamide compound to dithiocarbamate compound(s) is from 0.01/1 to 1/1 of the carboxamide compound/the dithiocarbamate compound(s).

The method of controlling plant disease according to the above [3] or [4], wherein the plant or the soil where a plan grows is wheat or the soil where wheat grows, respectively.

Advantageous Effect of Invention

According to the present invention, various plant diseases can be controlled.

DESCRIPTION OF EMBODIMENTS

The plant disease control composition of the present invention (hereinafter referred to as "composition") comprises a carboxamide compound represented by formula (I):

[Chem.3]

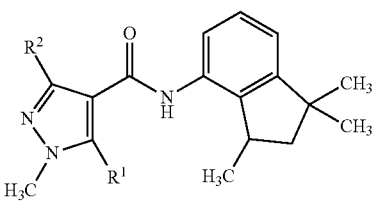

(I)

wherein
$R^1$ and $R^2$ represent the same meanings as defined in the above (hereinafter referred to as "carboxamide compound"), and one or more dithiocarbamate compounds selected from group (A) consisting of mancozeb, maneb, thiram and zineb (hereinafter referred to as dithiocarbamate compounds).

The "carboxamide compound" are those as described in, for example, WO86/02641 or WO92/12970 and can be prepared by the method described therein.

Particular examples of the "carboxamide compounds" are as follows:

carboxamide compound represented by formula (1):

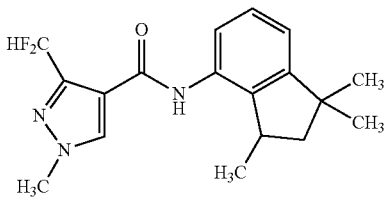

(1)

(hereinafter referred to as "carboxamide compound (1)"); carboxamide compound represented by formula (2):

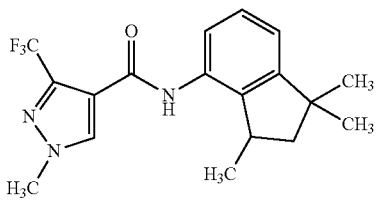

(2)

(hereinafter referred to as "carboxamide compound (2)"); carboxamide compound represented by formula (3):

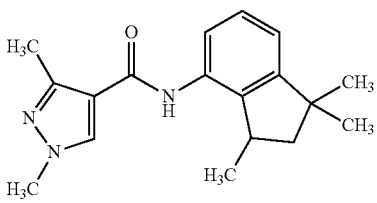

(3)

(hereinafter referred to as "carboxamide compound (3)"): carboxamide compound represented by formula (4):

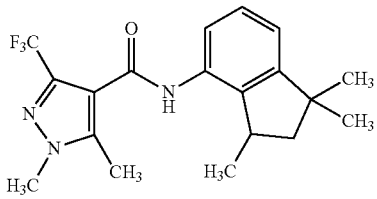

(4)

(hereinafter referred to as "carboxamide compound (4)"); carboxamide compound represented by formula (5):

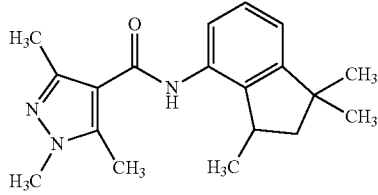

(5)

(hereinafter referred to as "carboxamide compound (5)").

The "dithiocarbamate compounds" are known compound and described in, for example, "THE PESTICIDE MANUAL—14th EDITION (published by BCPC) ISBN 1901396142 and WO 95/27693. These compounds can be obtained from the product containing said compound in the market or can be synthesized by publicly known method.

The weight ratio of the "carboxamide compound" to "dithiocarbamate compounds" in the "composition" is usually from 0.001/1 to 500/1, and preferably from 0.01/1 to 1/1 of "carboxamide compound"/"dithiocarbamate compound(s)".

Although the "composition" may be a mixture itself of a "carboxamide compound" and "dithiocarbamate compound(s)", the "composition" is usually prepared by mixing a "carboxamide compound", "dithiocarbamate compound(s)" and an inert carrier, and if necessary, by adding a surfactant and/or another auxiliary for formulation and by formulating the mixture into oil formulation, emulsifiable concentrate, flowable formulation, wettable powder, water dispersible granules, powder, granules, or the like.

The formulation, which is alone or by adding another inert component, can be used as a plant disease control agent.

The total content of a "carboxamide compound" and "dithiocarbamate compound(s)" in a "composition" is usually from 0.1% to 99% by weight, preferably from 0.2% to 90% by weight, and more preferably from 1% to 80% by weight.

Examples of the solid carriers used for the formulation include fine powder or granules of, for example, mineral materials such as kaolin clay, attapulgite, bentonite, montmorillonite, acid clay, pyrophillite, talc, diatomaceous earth and calcite; natural organic materials such as corncob powder and walnut powder; synthesized organic materials such as urea; salts such as potassium carbonate and ammonium sulfate; synthetic inorganic materials such as synthesized hydrous silicon oxide.

Examples of the liquid carriers include aromatic hydrocarbons such as xylene, alkylbenzene and methylnaphthalene; alcohols such as 2-propanol, ethylene glycol, propylene glycol and ethylene glycol mono-ethyl ether; ketones such as acetone, cyclohexanone and isophorone; vegetable oils such as soybean oil and cotton seed oil; petrolic aliphatic hydrocarbons; esters; dimethylsulfoxide; acetonitrile; and water. Examples of the surfactants include anionic surfactants such as alkyl sulfate ester salts, alkylarylsulfonate salts, dialkylsulfosuccinate salts, polyoxyethylene alkylaryl ether phosphoric acid ester salts, lignin sulfonate and naphthalene sulfonate formaldehyde polycondensed products; non-ionic surfactants such as polyoxyethylene alkyl aryl ethers, polyoxyethylene alkyl polyoxypropylene block copolymers and sorbitan fatty acid esters; and cationic surfactants such as alkyl trimethyl ammonium salts. Examples of the other auxiliaries for formulation include water-soluble polymers such as polyvinyl alcohol and polyvinylpyrrolidone; polysaccharides such as gum arabic, alginic acid and its salt, CMC (carboxymethylcellulose) and xanthan gum; inorganic materials such as aluminum magnesium silicate and alumina sol; preservatives; coloring agents; and stabilizers such as PAP (acidic isopropyl phosphate) and BHT.

The "composition" can be also prepared by formulating a "carboxamide compound" and "dithiocarbamate compound(s)" according to the method as described in the above, and then making the formulations or their diluents.

The "composition" can be used for protecting plant from plant disease.

Examples of plant diseases which can be controlled by the "composition" include the followings.

Rice diseases: *Magnaporthe grisea, Cochliobolus miyabeanus, Rhizoctonia solani, Gibberella fujikuroi*;

Wheat diseases: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Mycosphaerella graminicola, Stagonospora nodorum, Pyrenophora tritici-repentis*;

Barley diseases:

Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Rhizoctonia solani;

Maize diseases: *Ustilago maydis, Cochliobolus heterostrophus, Gloeocercospora sorghi, Puccinia polysora, Cercospora zeae-maydis, Rhizoctonia solani*;

Citrus diseases: *Diaporthe citri, Elsinoe fawcetti, Penicillium digitatum, P. italicum, Phytophthora parasitica, Phytophthora citrophthora*;

Apple diseases: *Monilinia mali, Valsa ceratosperma, Podosphaera leucotricha, Alternaria alternata apple pathotype, Venturia inaequalis, Colletotrichum acutatum, Phytophtora cactorum*;

Pear diseases: *Venturia nashicola, V. pirina, Alternaria alternata* Japanese pear pathotype, *Gymnosporangium haraeanum, Phytophtora cactorum*;

Peach diseases: *Monilinia fructicola, Cladosporium carpophilum, Phomopsis* sp.;

Grape diseases: *Elsinoe ampelina, Glomerella cingulata, Uninula necator, Phakopsora ampelopsidis, Guignardia bidwellii, Plasmopara viticola*;

Persimmon diseases: *Gloesporium kaki, Cercospora kaki, Mycosphaerela nawae*;

Gourd diseases: *Colletotrichum lagenarium, Sphaerotheca fuliginea, Mycosphaerella melonis, Fusarium oxysporum, Pseudoperonospora cubensis, Phytophthora* sp., *Pythium* sp.;

Tomato diseases: *Alternaria solani, Cladosporium fulvum, Phytophthora infestans*;

Eggplant diseases: *Phomopsis vexans, Erysiphe cichoracearum*; Brassicaceous vegetable diseases: *Alternaria japonica, Cercosporella brassicae, Plasmodiophora brassicae, Peronospora parasitica*;

Welsh onion diseases: *Puccinia allii, Peronospora destructor*;

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora casiicola, Sclerotinia sclerotiorum*;

Kidney bean diseases: *Colletrichum lindemthianum*;

Peanut diseases: *Cercospora personata, Cercospora arachidicola, Sclerotium rolfsii*;

Pea diseases pea: *Erysiphe pisi*;

Potato diseases: *Alternaria solani, Phytophthora infestans, Phytophthora erythroseptica, Spongospora subterranean*, f. sp. *Subterranean*;

Strawberry diseases: *Sphaerotheca humuli, Glomerella cingulata*;

Tea diseases: *Exobasidium reticulatum, Elsinoe leucospila, Pestalotiopsis* sp., *Colletotrichum theae-sinensis*;

Tobacco diseases: *Alternaria longipes, Erysiphe cichoracearum, Colletotrichum tabacum, Peronospora tabacina, Phytophthora nicotianae*;

Rapeseed diseases: *Sclerotinia sclerotiorum, Rhizoctonia solani*;

Cotton diseases: *Rhizoctonia solani*;

Beet diseases: *Cercospora beticola, Thanatephorus cucumeris, Thanatephorus cucumeris, Aphanomyces cochlioides*;

Rose diseases: *Diplocarpon rosae, Sphaerotheca pannosa, Peronospora sparsa*;

Diseases of chrysanthemum and asteraceae: *Bremia lactuca, Septoria chrysanthemiindici, Puccinia horiana*;

Diseases of various plants: *Pythium aphanidermatum, Pythium debarianum, Pythium graminicola, Pythium irregulare, Pythium ultimum, Botrytis cinerea, Sclerotinia sclerotiorum*;

Radish diseases: *Alternaria brassicicola*;

Zoysia diseases: *Sclerotinia homeocarpa, Rhizoctonia solani*;

Banana diseases: *Mycosphaerella fijiensis, Mycosphaerella musicola*;

Sunflower diseases: *Plasmopara halstedii*;

Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Rhoma* spp., *Rhizoctonia* spp., *Diplodia* spp., or the like;

Virus diseases of various plants mediated by *Polymixa* spp., *Olpidium* spp., or the like.

Examples of the plants for which the "composition" can be used include the followings:

Agricultural crops: maize, rice, wheat, barley, rye, oat, sorghum, cotton, soybean, peanut, buckwheat, sugar beet, rapeseed, sunflower, sugar cane, tobacco, and the like;

Vegetables: Solanaceous vegetables (eggplant, tomato, green pepper, hot pepper, potato, etc.), Cucurbitaceous vegetables (cucumber, pumpkin, zucchini, watermelon, melon, squash, etc.); Cruciferous vegetables (radish, turnip, horseradish, kohlrabi, Chinese cabbage, cabbage, brown mustard, broccoli, cauliflower, etc.), Asteraceous vegetables (burdock, garland chrysanthemum, artichoke, lettuce, etc.), Liliaceous vegetables (Welsh onion, onion, garlic, asparagus, etc.), Umbelliferous vegetables (carrot, parsley, celery, parsnip, etc.), Chenopodiaceous vegetables (spinach, chard, etc.), Lamiaceous vegetables (Japanese basil, mint, basil, etc.), strawberry, sweet potato, yam, aroid, and the like;

Flowering plants;

Ornamental foliage plants;

Turf;

Fruit trees: pome fruits (apple, common pear, Japanese pear, Chinese quince, quince, etc.), stone fruits (peach, plum, nectarine, Japanese plum, cherry, apricot, prune, etc.), citrus (mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut palm, and the like;

Trees other than fruit trees: tea, mulberry, flowering trees, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew), and the like.

The above-described plants may be those having resistance imparted by genetic engineering technique.

Among the above plants, the "composition" is expected to have excellent controlling effect particularly to plant diseases caused in wheat.

Among the above plant diseases, the diseases in wheat to which especially excellent effect of the "composition" can be expected are *Puccinia striiformis, P. graminis, P. recondita, Mycosphaerella graminicola, Stagonospora nodorum, Pyrenophora triticirepentis,* and the like.

Following compositions exemplify embodiments of the "composition":

a composition comprising "carboxamide compound (1)" and mancozeb;
a composition comprising "carboxamide compound (1)" and maneb;
a composition comprising "carboxamide compound (1)" and thiram;
a composition comprising "carboxamide compound (1)" and zineb;
a composition comprising "carboxamide compound (2)" and mancozeb;
a composition comprising "carboxamide compound (2)" and maneb;
a composition comprising "carboxamide compound (2)" and thiram;
a composition comprising "carboxamide compound (2)" and zineb;
a composition comprising "carboxamide compound (3)" and mancozeb;
a composition comprising "carboxamide compound (3)" and maneb;
a composition comprising "carboxamide compound (3)" and thiram;
a composition comprising "carboxamide compound (3)" and zineb;
a composition comprising "carboxamide compound (4)" and mancozeb;
a composition comprising "carboxamide compound (4)" and maneb;
a composition comprising "carboxamide compound (4)" and thiram;
a composition comprising "carboxamide compound (4)" and zineb;
a composition comprising "carboxamide compound (5)" and mancozeb;
a composition comprising "carboxamide compound (5)" and maneb;
a composition comprising "carboxamide compound (5)" and thiram;
a composition comprising "carboxamide compound (5)" and zineb;
a composition comprising "carboxamide compound (1)" and mancozeb in which the weight ratio of "carboxamide compound (1)" to mancozeb is 0.01/1 to 1/1;
a composition comprising "carboxamide compound (1)" and maneb in which the weight ratio of "carboxamide compound (1)" to maneb is 0.01/1 to 1/1;
a composition comprising "carboxamide compound (1)" and thiram in which the weight ratio of "carboxamide compound (1)" to thiram is 0.01/1 to 1/1;
a composition comprising "carboxamide compound (1)" and zineb in which the weight ratio of "carboxamide compound (1)" to zineb is 0.01/1 to 1/1;
a composition comprising "carboxamide compound (2)" and mancozeb in which the weight ratio of "carboxamide compound (2)" to mancozeb is 0.01/1 to 1/1;
a composition comprising "carboxamide compound (2)" and maneb in which the weight ratio of "carboxamide compound (2)" to maneb is 0.01/1 to 1/1;
a composition comprising "carboxamide compound (2)" and thiram in which the weight ratio of "carboxamide compound (2)" to thiram is 0.01/1 to 1/1;
a composition comprising "carboxamide compound (2)" and zineb in which the weight ratio of "carboxamide compound (2)" to zineb is 0.01/1 to 1/1;
a composition comprising "carboxamide compound (3)" and mancozeb in which the weight ratio of "carboxamide compound (3)" to mancozeb is 0.01/1 to 1/1;
a composition comprising "carboxamide compound (3)" and maneb in which the weight ratio of "carboxamide compound (3)" to maneb is 0.01/1 to 1/1;
a composition comprising "carboxamide compound (3)" and thiram in which the weight ratio of "carboxamide compound (3)" to thiram is 0.01/1 to 1/1;
a composition comprising "carboxamide compound (3)" and zineb in which the weight ratio of "carboxamide compound (3)" to zineb is 0.01/1 to 1/1;
a composition comprising "carboxamide compound (4)" and mancozeb in which the weight ratio of "carboxamide compound (4)" to mancozeb is 0.01/1 to 1/1;
a composition comprising "carboxamide compound (4)" and maneb in which the weight ratio of "carboxamide compound (4)" to maneb is 0.01/1 to 1/1;
a composition comprising "carboxamide compound (4)" and thiram in which the weight ratio of "carboxamide compound (4)" to thiram is 0.01/1 to 1/1;
a composition comprising "carboxamide compound (4)" and zineb in which the weight ratio of "carboxamide compound (4)" to zineb is 0.01/1 to 1/1;
a composition comprising "carboxamide compound (5)" and mancozeb in which the weight ratio of "carboxamide compound (5)" to mancozeb is 0.01/1 to 1/1;
a composition comprising "carboxamide compound (5)" and maneb in which the weight ratio of "carboxamide compound (5)" to maneb is 0.01/1 to 1/1;
a composition comprising "carboxamide compound (5)" and thiram in which the weight ratio of "carboxamide compound (5)" to thiram is 0.01/1 to 1/1;
a composition comprising "carboxamide compound (5)" and zineb in which the weight ratio of "carboxamide compound (5)" to zineb is 0.01/1 to 1/1;

The method for controlling plant disease (hereinafter referred to as "controlling method") can be carried out by treating a plant or the soil where a plan grows with an effective amount of a "carboxamide compound" and "dithiocarbamate compound(s)".

The part of plant to be treated is stem and leaf of a plant, seed or bulb of a plant, and the bulb means bulb, corm, rootstock, tuber, tuberous root and rhizophore.

In the "controlling method", the treatment of a plant or the soil where a plan grows with a "carboxamide compound" and "dithiocarbamate compound(s)" can be carried out separately at the same timing, but the treatment is usually carried out by using a "composition" in light of convenience.

In the "controlling method", the treatment with a "carboxamide compound" and "dithiocarbamate compound(s)" is, for example, stems and leaves application, soil application, roots application or seeds application.

Examples of the stems and leaves application include a treatment for surface of cultivated plant by a stem and leave spray or a stem and tree spray.

Examples of the root application include a method of dipping a whole plant or root of a plant into a liquid containing a "carboxamide compound" and "dithiocarbamate compound(s)" and a method of sticking a solid preparation comprising a "carboxamide compound", "dithiocarbamate compound(s)" and a solid carrier onto root of a plant.

Examples of the soil application include a method of spraying a "composition" onto the soil, a method of mixing a "composition" with a soil and a method of irrigating a "composition" into the soil.

Examples of the seed application include a method of treating seeds or bulbs of a plant to be protected from a plant disease with a "composition". Particularly, the application can be carried out by spraying a suspension of a "composition" to the surface of seeds or bulbs, or by spreading wettable powder, emulsifiable concentrate or flowable formulation itself or a mixture thereof with a small amount of water on the seeds or the bulbs, or by dipping the seeds into a solution of a "composition" for a prescribed time, or by film coating application or pellet coating application.

The amount of a "carboxamide compound" and "dithiocarbamate compound(s)" used in the "controlling method" is different depending on the kind of a plant to be treated, the kind of a plant disease to be controlled and its frequency, the kind of a formulation, timing of treatment, method of treatment, place of treatment, weather condition, and the like.

When a "composition" is applied to stems and/or leaves of a plant or to the soil where a plan grows, the total amount of a "carboxamide compound" and "dithiocarbamate compound(s)" is usually from b 1 g to 500 g/1000 m$^2$, preferably from 2 g to 200 g/1000 m$^2$, and more preferably from 10 g to 100 g/1000 m$^2$.

When a "composition" is applied to seeds of a plant, the total amount of a "carboxamide compound" and "dithiocarbamate compound(s)" is usually from 0.001 g to 10 g/1 kg of the seeds, and preferably from 0.01 g to 1 g/1 kg of the seeds.

An emulsifiable concentrate, wettable powder or flowable formulation is usually used by diluting the formulation with water and spraying the diluted formulation. In this case, the concentration of a "carboxamide compound" and "dithiocarbamate compound(s)" in total of the diluted formulation is usually from 0.0005 to 2% by weight and preferably from 0.005 to 1% by weight.

A powder formulation, granule formulation, and the like is usually used without dilution.

EXAMPLE

The present invention is further explained in detail with Formulation Examples and Test Examples. However, the present invention is not limited by the following Examples.

In the following Examples, "part" means "part by weight" unless otherwise provided.

Formulation Example 1

One of "carboxamide compounds" (1) to (5) (2 part), mancozeb (8 parts), a mixture of white carbon and polyoxyethylene alkyl ether sulfate ammonium salt (weight ratio 1:1) (35 parts) and water (55 parts) are mixed and milled by wet-milling method to give each of formulations, respectively.

Formulation Example 2

One of "carboxamide compounds" (1) to (5) (2 part), maneb (8 parts), a mixture of white carbon and polyoxyethylene alkyl ether sulfate ammonium salt (weight ratio 1:1) (35 parts) and water (55 parts) are mixed and milled by wet-milling method to give each of formulations, respectively.

Formulation Example 3

One of "carboxamide compounds" (1) to (5) (2 part), thiram (8 parts), a mixture of white carbon and polyoxyethylene alkyl ether sulfate ammonium salt (weight ratio 1:1) (35 parts) and water (55 parts) are mixed and milled by wet-milling method to give each of formulations, respectively.

Formulation Example 4

One of "carboxamide compounds" (1) to (5) (2 part), zineb (8 parts), a mixture of white carbon and polyoxyethylene alkyl ether sulfate ammonium salt (weight ratio 1:1) (35 parts) and water (55 parts) are mixed and milled by wet-milling method to give each of formulations, respectively.

Formulation Example 5

One of "carboxamide compounds" (1) to (5) (3 parts), mancozeb (12 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminum magnesium silicate (0.1 part), and further propylene glycol (10 parts) is added to the mixture. The resultant mixture is mixed by stirring to give each of formulations, respectively.

Formulation Example 6

One of "carboxamide compounds" (1) to (5) (3 parts), maneb (12 parts), sorbitan trioleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminum magnesium silicate (0.1 part), and further propylene glycol (10 parts) is added to the mixture. The resultant mixture is mixed by stirring to give each of formulations, respectively.

Formulation Example 7

One of "carboxamide compounds" (1) to (5) (3 parts), thiram (12 parts), sorbitan trioleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminum magnesium silicate (0.1 part), and further propylene glycol (10 parts) is added to the mixture. The resultant mixture is mixed by stirring to give each of formulations, respectively.

Formulation Example 8

One of "carboxamide compounds" (1) to (5) (3 parts), zineb (12 parts), sorbitan trioleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminum magnesium silicate (0.1 part), and further propylene glycol (10 parts) is added to the mixture. The resultant mixture is mixed by stirring to give each of formulations, respectively.

Formulation Example 9

One of "carboxamide compounds" (1) to (5) (1 part), mancozeb (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 10

One of "carboxamide compounds" (1) to (5) (1 part), maneb (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 11

One of "carboxamide compounds" (1) to (5) (1 part), thiram (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 12

One of "carboxamide compounds" (1) to (5) (1 part), zineb (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 13

One of "carboxamide compounds" (1) to (5) (12.5 parts), mancozeb (37.5 parts), calcium ligninsulfonate (3 parts), sodium lauryl sulfate (2 parts) and synthesized hydrous silicon oxide (45 parts) are thoroughly mixed and milled to give each of formulations, respectively.

Formulation Example 14

One of "carboxamide compounds" (1) to (5) (3 parts), mancozeb (2 parts), kaolin clay (85 parts) and talc (10 parts) are thoroughly mixed and milled to give each of formulations, respectively.

Test Examples using each of the "compositions" are shown in the following.

Test Example 1

Each plastic pot was filled with soil, and seeds of wheat (variety: Apogee) were seeded in the soil followed by growing for 14 days in a greenhouse. Test compounds were formulated into formulations according to Formulation Example 5, and the formulation was diluted with water to prescribed concentration. Foliar application of the dilution was carried out so that dilution would adhere to surface of leaves of the wheat sufficiently. After spraying, the plant was air-dried and two days after, the plant was inoculated by spraying aqueous suspension of conidiospores of Mycosphaerella graminicola (about 1,000,000/ml). After the inoculation, the plants were placed under high humidity condition at 18° C. for 3 days, taken out from the high humidity condition and then placed in a thermostatic room at 18° C. for 14 days (hereinafter referred to as "treated plot"). Thereafter, the lesion area by Mycosphaerella graminicola was investigated.

On the other hand, wheat was grown in the same way as above "treated plot" except for that the dilution of the test compound was not applied to the stems and leaves (hereinafter referred to as "non-treated plot"). The lesion area by Mycosphaerella graminicola was investigated as above "treated plot".

On the basis of the above lesion areas in "treated plot" and "non-treated plot", efficacy in "treated plot" was evaluated by the following calculation formula (1). The results are shown in Table 1 and Table 2.

Efficacy (%)=[1−(lesion area in "treated plot"/lesion area in "non-treated plot")]×100     Calculation Formula (1)

TABLE 1

| "carboxamide compound (1)" [ppm] | mancozeb [ppm] | efficacy (%) |
| --- | --- | --- |
| 50 | 700 | 100 |

TABLE 2

| "carboxamide compound (5)" [ppm] | mancozeb [ppm] | efficacy (%) |
| --- | --- | --- |
| 50 | 700 | 100 |

INDUSTRIAL APPLICABILITY

A plant disease control composition comprising a "carboxamide compound" represented by formula (I) and a dithiocarbamate compound is useful for controlling plant disease.

The invention claimed is:
1. A plant disease control composition comprising a carboxamide compound represented by formula (I):

(I)

and mancozeb,
wherein the weight ratio of the carboxamide compound to mancozeb is from 0.01/1 to 1/1 of the carboxamide compound/mancozeb.

2. A method of controlling plant disease which comprises a step of treating a plant or the soil where a plant grows with an effect amount of a carboxamide compound represented by formula (1):

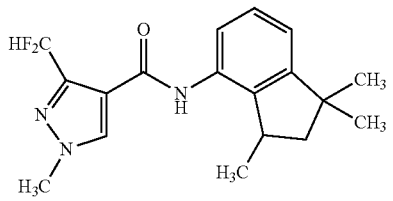

(I)

and mancozeb,
wherein the weight ratio of the carboxamide compound to mancozeb is from 0.01/1 to 1/1 of the carboxamide compound/mancozeb.

3. The method of controlling plant disease according to claim 2 wherein the plant or the soil where a plant grows is wheat or the soil where wheat grows, respectively.

* * * * *